(12) United States Patent
Locke et al.

(10) Patent No.: US 9,693,907 B2
(45) Date of Patent: Jul. 4, 2017

(54) INCISIONAL ABSORBENT DRESSING

(71) Applicant: KCI Licensing, Inc., San Antonio, TX (US)

(72) Inventors: Christopher Brian Locke, Bournemouth (GB); Colin John Hall, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 484 days.

(21) Appl. No.: 13/954,562

(22) Filed: Jul. 30, 2013

(65) Prior Publication Data

US 2014/0031771 A1 Jan. 30, 2014

Related U.S. Application Data

(60) Provisional application No. 61/677,376, filed on Jul. 30, 2012.

(51) Int. Cl.
*A61M 27/00* (2006.01)
*A61F 13/00* (2006.01)
(Continued)

(52) U.S. Cl.
CPC .. *A61F 13/00068* (2013.01); *A61F 13/00987* (2013.01); *A61F 13/022* (2013.01);
(Continued)

(58) Field of Classification Search
CPC .............. A61F 13/0216; A61F 13/0203; A61F 13/0206; A61F 13/022; A61M 1/0088
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 745271 4/1999
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96.
(Continued)

*Primary Examiner* — Jacqueline Stephens

(57) ABSTRACT

Dressings, systems, and methods are disclosed, in some embodiments, that involve treating a tissue site with reduced pressure. In one embodiment, a reduced-pressure dressing may include a dressing bolster, a retention pouch, and a sealing member. The dressing bolster may be adapted to apply a compressive force to the tissue site capable of closing a wound or incision therein. The retention pouch may be adapted to retain and manage fluid extracted from the tissue site to keep the tissue site substantially free of fluid and to prevent clogging of the reduced-pressure dressing. The sealing member may provide a seal over the retention pouch, the dressing bolster, and a portion of the epidermis of the patient. Other dressings, systems, and methods are disclosed.

29 Claims, 11 Drawing Sheets

(51) Int. Cl.
*A61M 1/00* (2006.01)
*A61F 13/02* (2006.01)

(52) U.S. Cl.
CPC ....... *A61F 13/0209* (2013.01); *A61M 1/0023* (2013.01); *A61M 1/0027* (2014.02); *A61F 13/0203* (2013.01); *A61F 13/0206* (2013.01); *A61F 13/0216* (2013.01); *A61F 2013/00174* (2013.01); *A61M 1/0088* (2013.01); *Y10T 156/10* (2015.01)

(58) Field of Classification Search
USPC ................................................ 604/543, 540
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,308,896 A | 5/1994 | Hansen |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2009/0227969 A1* | 9/2009 | Jaeb .......... A61M 1/0088 604/313 |
| 2010/0125258 A1* | 5/2010 | Coulthard ......... A61F 13/0203 604/319 |

FOREIGN PATENT DOCUMENTS

| | | |
|---|---|---|
| AU | 755496 | 2/2002 |
| CA | 2005436 | 6/1990 |
| CN | 102046119 A | 5/2011 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |

(56) References Cited

FOREIGN PATENT DOCUMENTS

| WO | 97/18007 | 5/1997 |
|---|---|---|
| WO | 99/13793 | 3/1999 |
| WO | 2009/146441 A1 | 12/2009 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, Md., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Dukić, Ž. Maksimović, D. Radak, and P. Peška, "Vacuum Therapy in the Treatment of Peripheral Blood Vessels," Timok Medical Journal 11 (1986), pp. 161-164.
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).
International Search Report for PCT/US2013/052733 issued Feb. 10, 2013.
European Examination Report for corresponding European Application No. EP13745555.6 dated Jul. 15, 2016.

* cited by examiner

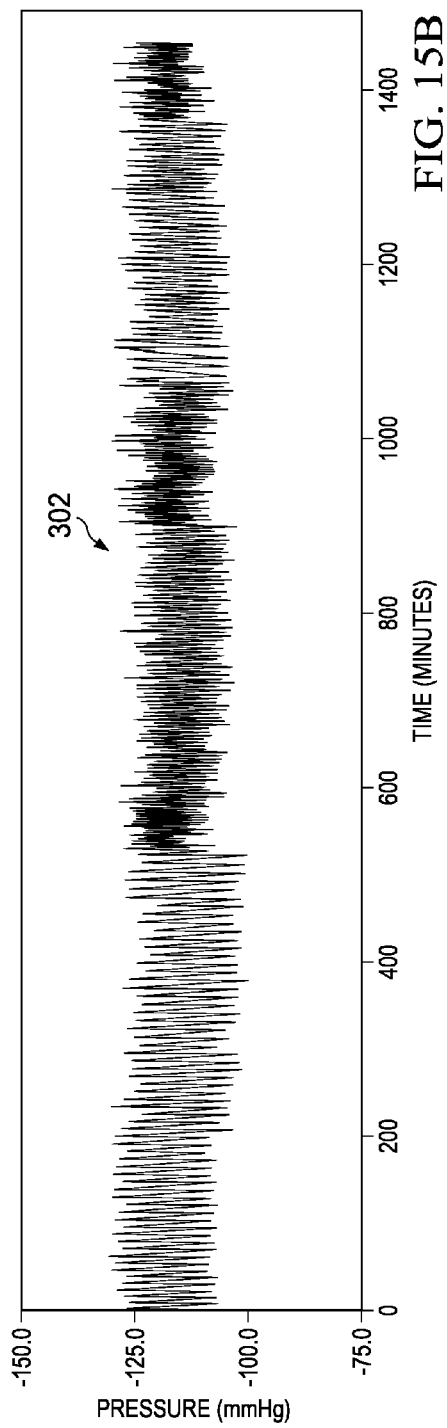
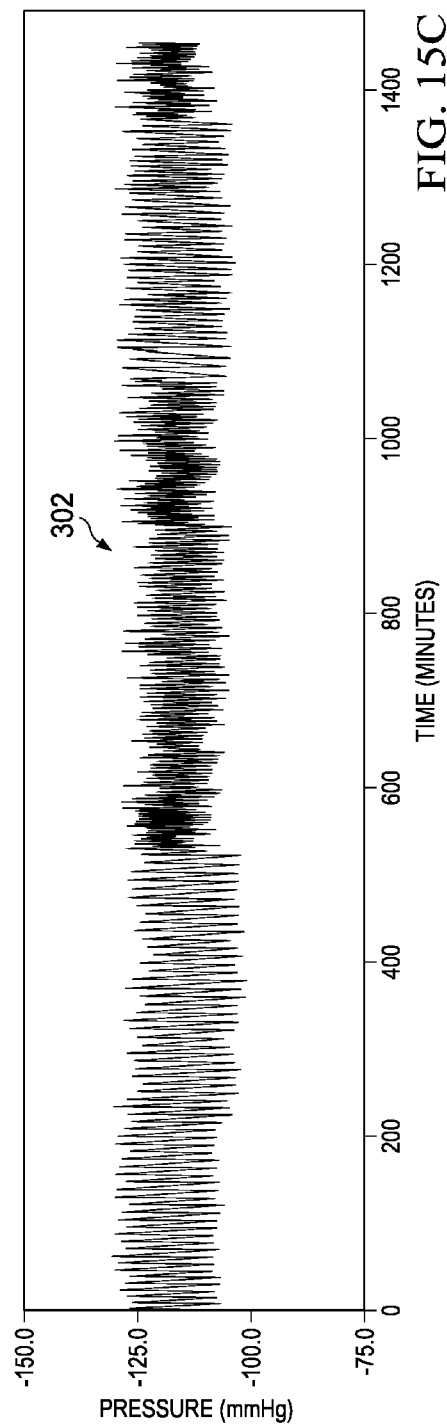

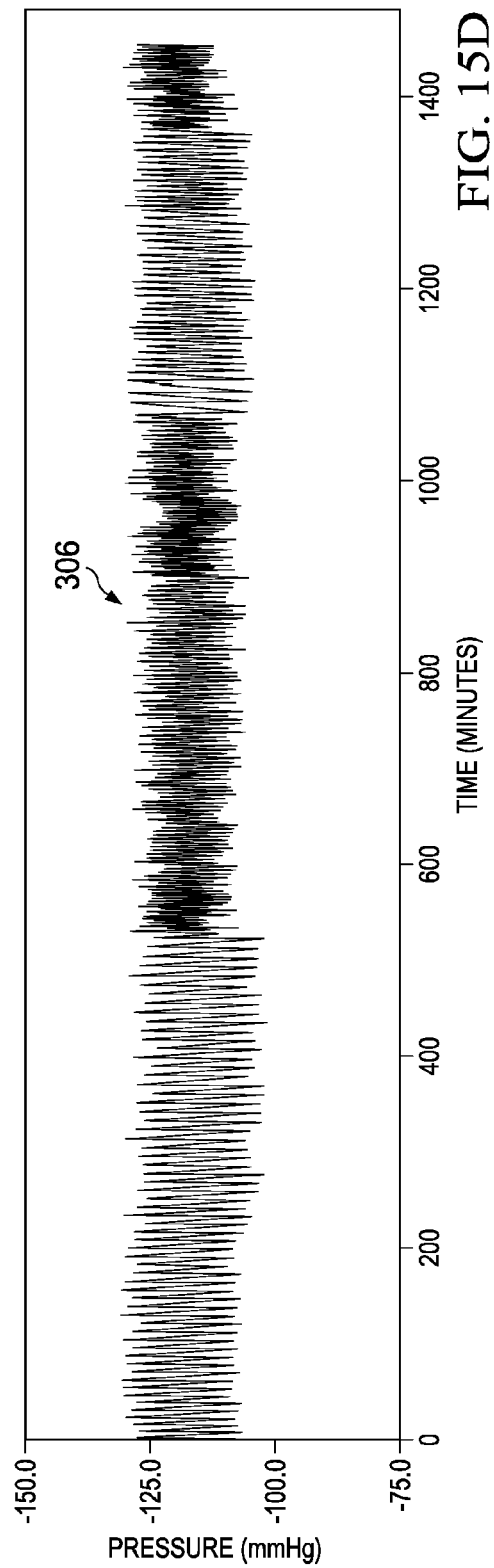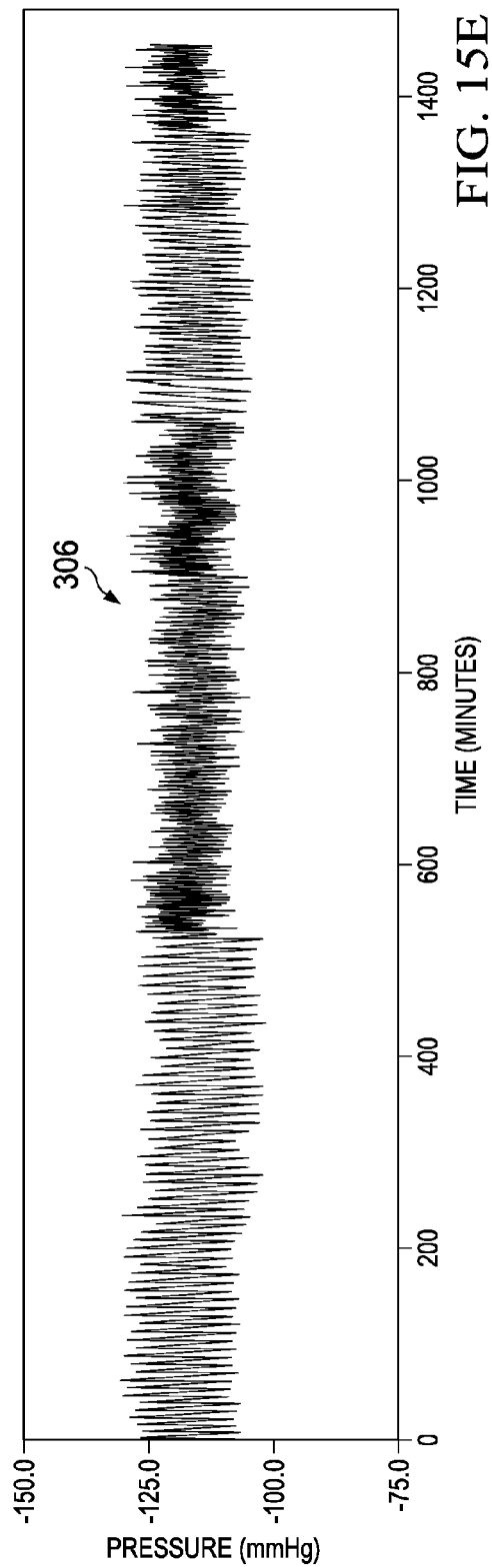

INCISIONAL ABSORBENT DRESSING

RELATED APPLICATION

This application claims the benefit, under 35 USC §119(e), of the filing of U.S. Provisional Patent Application Ser. No. 61/677,376, entitled "INCISIONAL ABSORBENT DRESSING," filed 30 Jul. 2012, which is incorporated herein by reference for all purposes.

BACKGROUND

This disclosure relates generally to medical wound care systems, and more particularly, but not by way of limitation, to reduced-pressure incisional absorbent dressings, systems, and methods.

Depending on the medical circumstances, reduced pressure may be used for, among other things, reduced-pressure therapy to encourage granulation at a tissue site, draining fluids at a tissue site, closing a wound, reducing edema, promoting perfusion, or fluid management.

Common dressings, systems, and methods typically include tubing, external canisters, and other components for providing reduced-pressure therapy. These components may be cumbersome for the patient, expensive, and prone to leaking and blockages. Further, the dressing and associated components may require a particular orientation and installation in order for the patient to receive effective therapy. Thus, improvements that enhance patient comfort and usability while maintaining or exceeding current treatment capabilities are desirable.

SUMMARY

Shortcomings with certain aspects of tissue treatment methods, dressings, and systems are addressed by this disclosure as shown and described in a variety of illustrative, non-limiting embodiments herein.

According to an illustrative, non-limiting embodiment, a reduced-pressure dressing for treating a tissue site on a patient with reduced pressure includes a dressing bolster, a retention pouch, a sealing member, and a reduced-pressure interface. The dressing bolster is adapted to be positioned proximate to the tissue site, between the tissue site and the retention pouch. The retention pouch is adapted to retain a fluid. The sealing member is adapted to cover the retention pouch, the dressing bolster, and a portion of the epidermis of the patient that is proximate to the tissue site. The reduced-pressure interface is coupled to the sealing member for providing fluid communication to the reduced-pressure dressing.

According to another illustrative, non-limiting embodiment, a system for treating a tissue site on a patient with reduced pressure includes a reduced-pressure dressing, a reduced-pressure source, and a reduced-pressure delivery conduit. The reduced-pressure dressing includes a dressing bolster, a retention pouch, a sealing member, and a reduced-pressure interface. The dressing bolster has a first side and a second side. The first side of the dressing bolster faces opposite the second side and is adapted to be positioned facing the tissue site. The retention pouch is adapted to retain a fluid and is positioned proximate to the second side of the dressing bolster. The retention pouch includes a first permeable layer, a second permeable layer, and an absorbent core. The absorbent core is encapsulated between the first and the second permeable layers. The sealing member is adapted to cover the retention pouch, the dressing bolster, and a portion of the epidermis of the patient that is proximate to the tissue site. The reduced-pressure interface is coupled to the sealing member and provides fluid communication to the reduced-pressure dressing. The reduced-pressure delivery conduit fluidly couples the reduced-pressure source to the reduced-pressure interface.

According to another illustrative, non-limiting embodiment, a method of manufacturing a dressing for use with reduced pressure to treat a tissue site on a patient includes the steps of: providing a dressing bolster having a first side and a second side, the first side facing opposite the second side, wherein the dressing bolster is adapted to distribute reduced pressure to the tissue site and to contract upon application of reduced pressure; positioning a retention pouch proximate to the second side of the dressing bolster, wherein the retention pouch is adapted to retain a fluid; positioning a sealing member over the dressing bolster and the retention pouch, wherein a portion of the sealing member is adapted to sealingly engage the epidermis of a patient proximate to the tissue site; fluidly coupling a reduced-pressure source to the sealing member, wherein the reduced pressure source is in fluid communication with the dressing bolster and the retention pouch.

Other features and advantages of the illustrative embodiments will become apparent with reference to the drawings and detailed description that follow.

BRIEF DESCRIPTION OF THE DRAWINGS

A more complete understanding of this disclosure may be obtained by reference to the following Detailed Description when taken in conjunction with the accompanying drawings wherein:

FIGS. 15A-15E provide charts illustrating reduced pressure measured at four locations over time in an illustrative embodiment of a reduced-pressure dressing according to this disclosure.

DETAILED DESCRIPTION

In the following Detailed Description of the non-limiting, illustrative embodiments, reference is made to the accompanying drawings that form a part hereof. Other embodiments may be utilized, and logical, structural, mechanical, electrical, and chemical changes may be made without departing from the scope of this disclosure. To avoid detail not necessary to enable those skilled in the art to practice the embodiments described herein, the Description may omit certain information known to those skilled in the art. Thus, the following Detailed Description is provided without limitation and with the scope of the illustrative embodiments being defined by the appended claims. Further, as used throughout the Description and unless otherwise indicated, "or" does not require mutual exclusivity.

Figure 1:
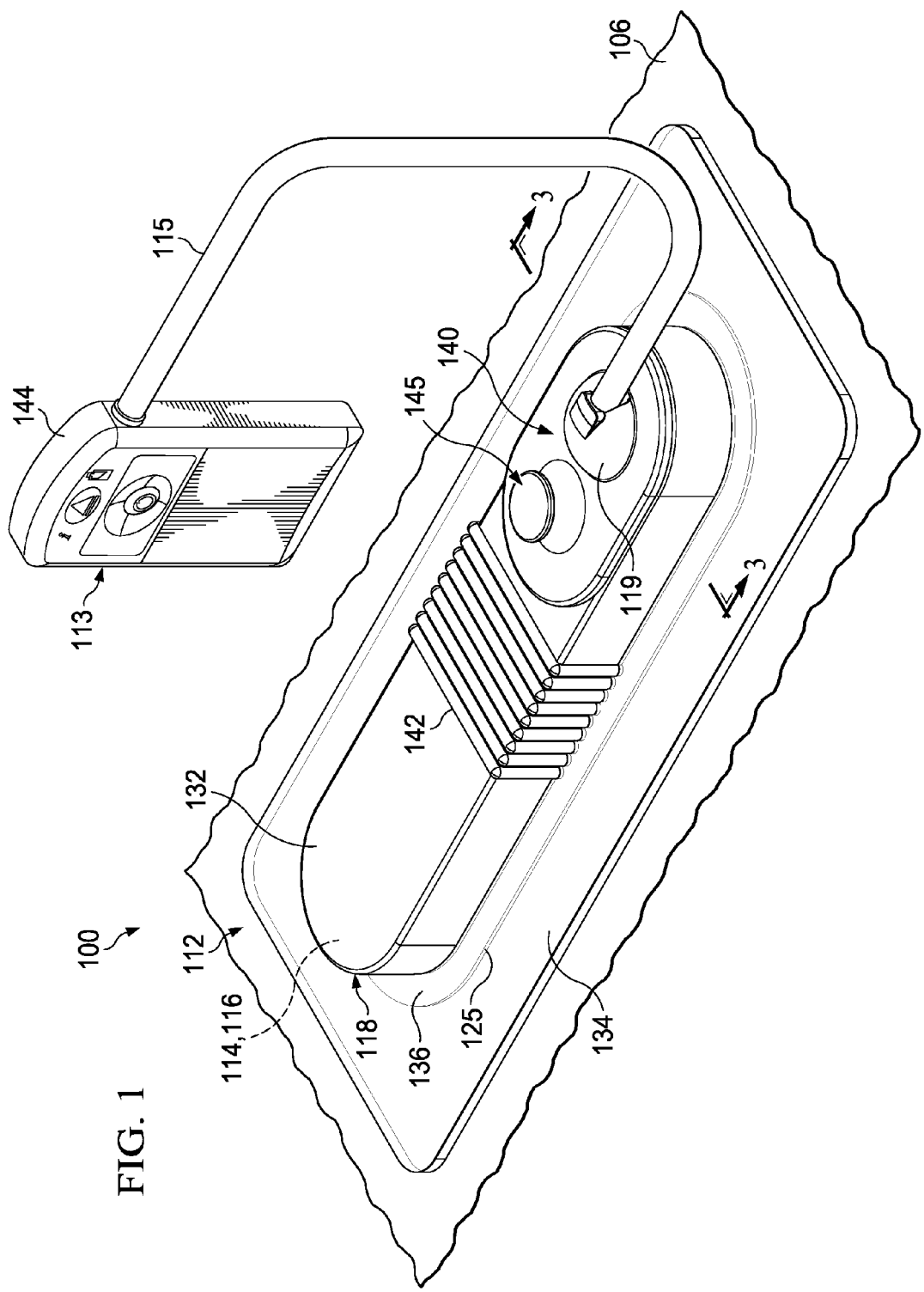
FIG. 1 is a perspective view of an illustrative embodiment of a system for treating a tissue site on a patent.
Figure 2:
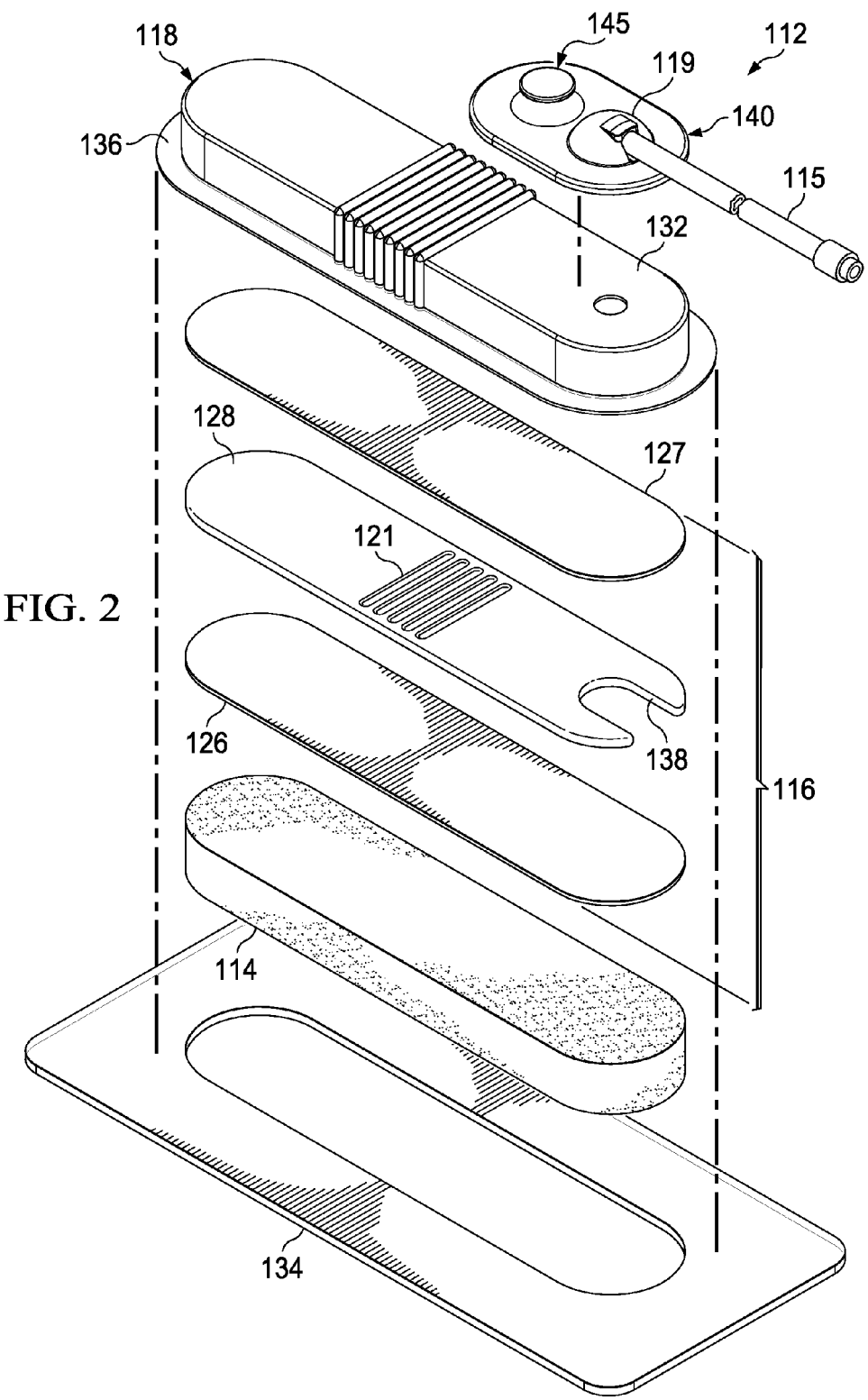
FIG. 2 is a perspective, exploded view of an illustrative embodiment of a reduced-pressure dressing depicted in FIG. 1.
Figure 3:
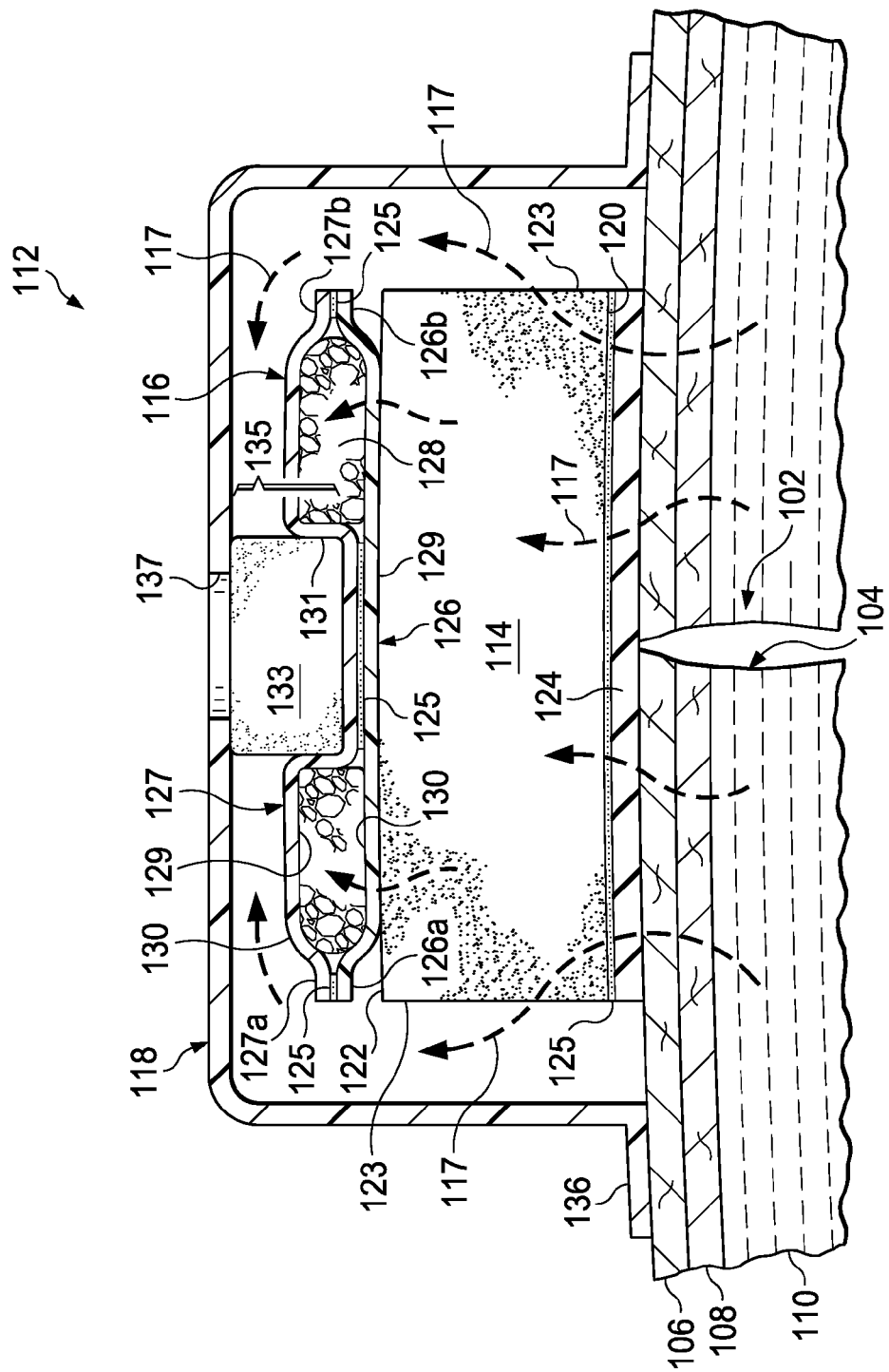
FIG. 3 is a cross-section view of the reduced-pressure dressing of FIG. 1, taken along line 3-3 in FIG. 1.
Figure 4:
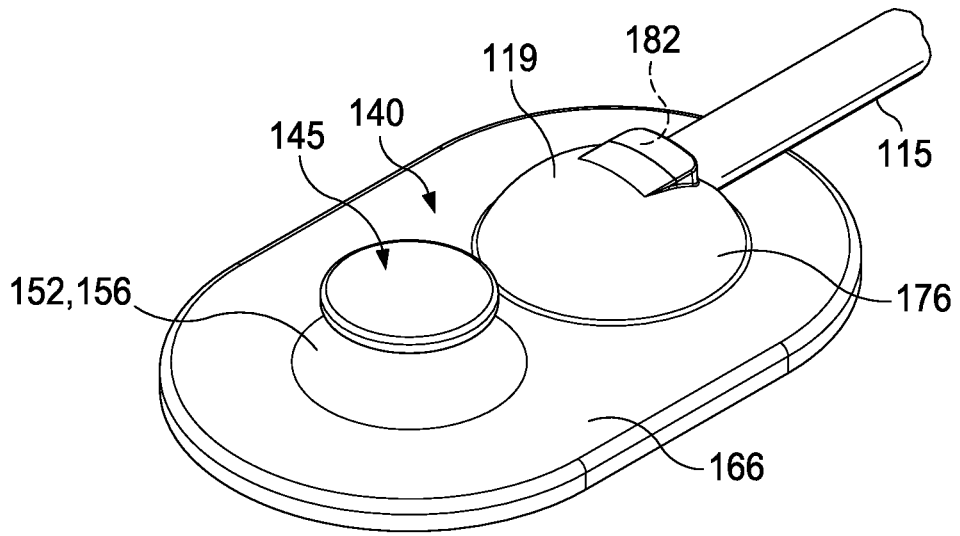
FIG. 4 is a perspective view of an illustrative embodiment of a reduced-pressure assembly depicted in FIG. 1.
Figure 5A:
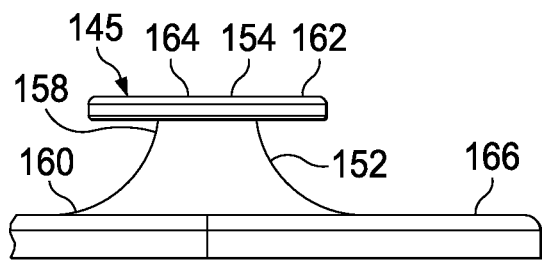
FIG. 5A is an elevation view of a portion of an illustrative embodiment of a fluid capacity indicator depicted in FIG. 1, shown in an extended position.
Figure 5B:
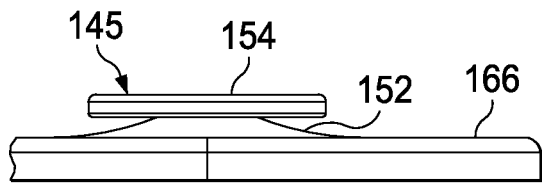
FIG. 5B is an elevation view of a portion of an illustrative embodiment of a fluid capacity indicator depicted in FIG. 1, shown in a retracted position.
Figure 6:
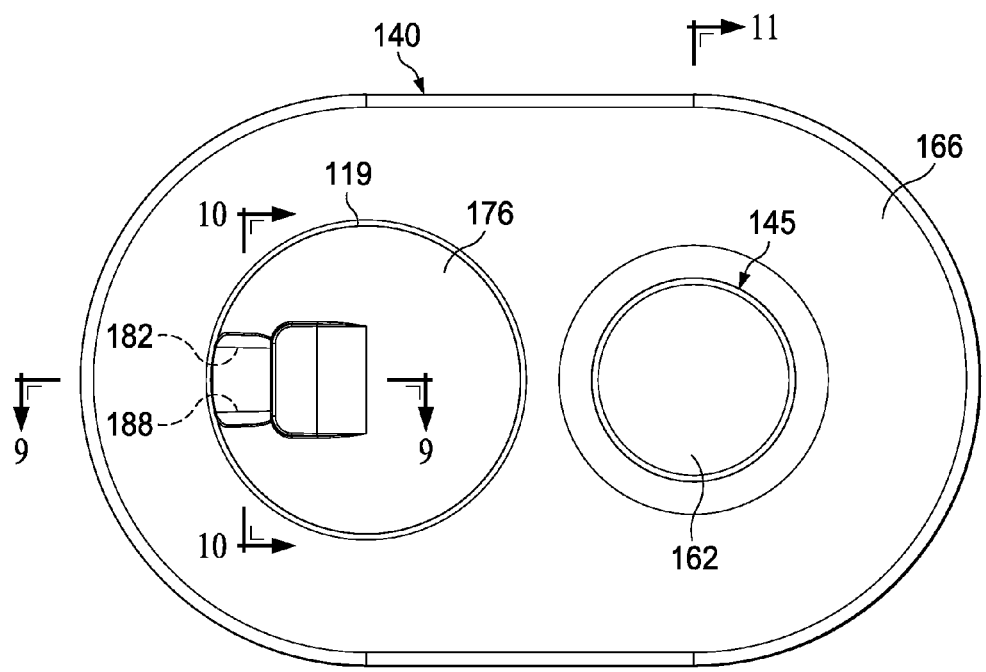
FIG. 6 is a top view of the reduced-pressure assembly of FIG. 4.
Figure 7:
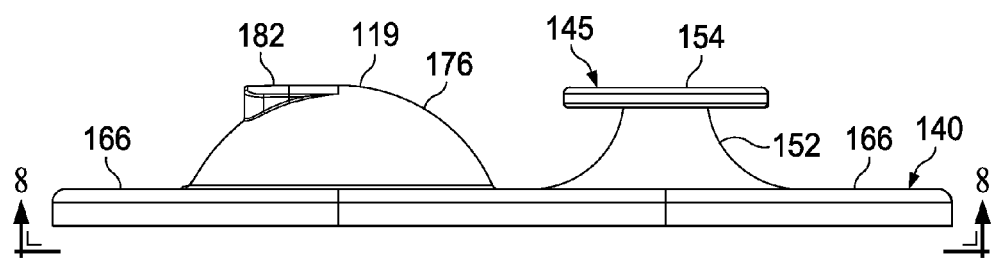
FIG. 7 is a side view of the reduced-pressure assembly of FIG. 4.
Figure 8:
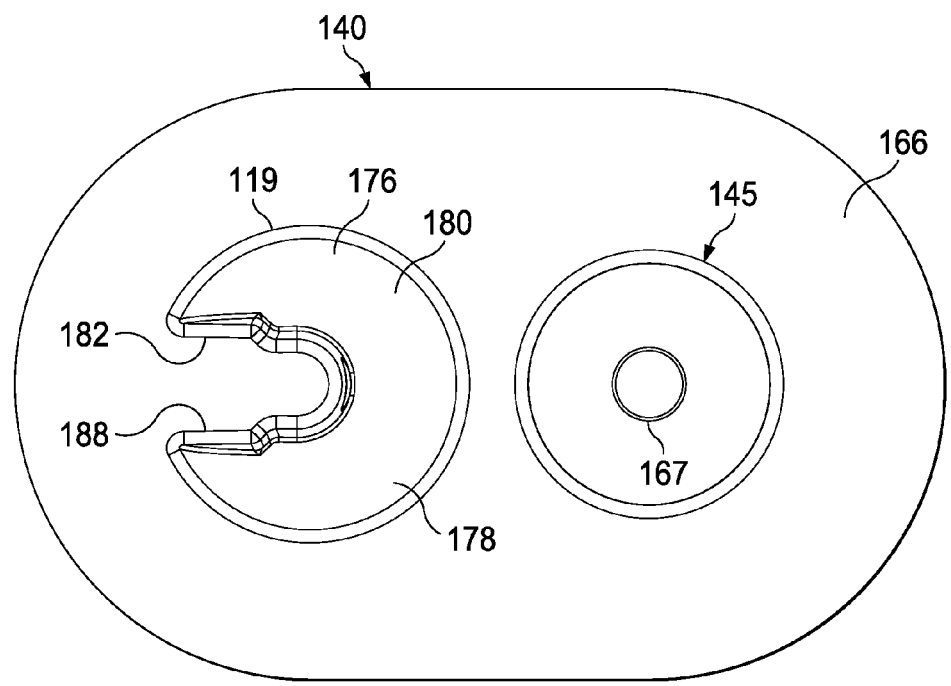
FIG. 8 is a bottom view of the reduced-pressure assembly of FIG. 4 taken along line 8-8 in FIG. 7.

Referring to the drawings, FIGS. 1-3 depict an embodiment of a reduced-pressure treatment system 100 for treating a tissue site 102, such as, for example, an incision 104. The incision 104 may extend through or otherwise involve an epidermis 106, a dermis 108, and a subcutaneous tissue 110. The reduced-pressure treatment system 100 may also be used at other tissue sites.

The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. The treatment of the tissue site 102 may include removal of fluids such as exudate or ascites.

The reduced-pressure treatment system 100 may include a reduced-pressure dressing 112, a reduced-pressure subsystem 113, and a reduced-pressure delivery conduit 115. The reduced-pressure delivery conduit 115 may provide reduced pressure from the reduced-pressure subsystem 113 to the reduced-pressure dressing 112.

In one embodiment, the reduced-pressure dressing 112 may include a dressing bolster 114, a retention pouch 116, a sealing member 118, and a reduced pressure interface 119. While the reduced-pressure system 100 is shown in FIG. 3 in the context of the reduced-pressure dressing 112 over an incision 104, the reduced-pressure treatment system 100 may be used on other tissue sites, including open wounds. Further, the dressing bolster 114 and the retention pouch 116 described herein may be deployed in place of a fluid distribution manifold used in connection with other types of reduced-pressure treatment systems. Thus, this disclosure is not limited to the particular embodiments of the reduced-pressure treatment system 100 described herein.

The dressing bolster 114 has a first side 120, a second side 122, and edges 123. The first side 120 and the second side 122 may terminate at edges 123 and face in opposite directions from one another. The first side 120 of the dressing bolster 114 may be adapted to face inward toward the tissue site 102. The dressing bolster 114 may include a plurality of flexibility notches or recesses (not shown) that may be lateral cuts in the dressing bolster 114. The dressing bolster 114 may include one or more longitudinal cuts or other cuts. The flexibility notches may enhance the flexibility of the dressing bolster 114. The enhanced flexibility may be useful when the reduced-pressure dressing 112 is applied over a joint or other area of movement.

The dressing bolster 114 may be formed from any flexible bolster material or manifold material that provides a vacuum space or treatment space, such as, for example, a porous and permeable foam or foam-like material, a member formed with pathways, a graft, a gauze, or other similar material. As a more specific, non-limiting example, the dressing bolster 114 may be a reticulated, open-cell polyurethane or polyether foam that allows good permeability of wound fluids while under a reduced pressure. One such foam material is the VAC® GranuFoam® material available from Kinetic Concepts, Inc. (KCI) of San Antonio, Tex. Any material or combination of materials may be used as a manifold material for the dressing bolster 114 provided that the manifold material is operable to distribute reduced pressure. The term "manifold" as used herein generally refers to a substance or structure provided to assist in applying reduced pressure to, delivering fluids to, or removing fluids from a tissue site. A manifold may include a plurality of flow channels or pathways. The plurality of flow channels may be interconnected to improve the distribution of fluids provided to and removed from the area of tissue around the manifold. Examples of manifolds may include, without limitation, devices that have structural elements arranged to form flow channels, cellular foam, such as open-cell foam, porous tissue collections, and liquids, gels, and foams that include or cure to include flow channels.

A material with a higher or lower density, or a smaller or larger pore size than GranuFoam® material may be desirable for the dressing bolster 114 depending on the application. Among the many possible materials, the following may be used: GranuFoam® material; Foamex® technical foam (www.foamex.com); molded bed of nails structures; patterned grid material, such as those manufactured by Sercol Industrial Fabrics; 3D textiles, such as those manufactured by Baltex of Derby, U.K.; a gauze, a flexible channel-containing member; a graft; or similar material. Ionic silver may be added to the foam in a micro bonding process. Other substances may also be added to the foam, such as antimicrobial agents.

In one embodiment, the dressing bolster 114 may be a hydrophobic layer. The hydrophobic characteristics of the dressing bolster 114 may prevent the dressing bolster 114 from directly absorbing fluid, such as exudate, from the tissue site 102, but allow the fluid to pass through. Thus, as depicted by the fluid communication arrows 117 in FIG. 3, the fluid may be drawn away from the tissue site 102 using a reduced pressure source, such as the reduced pressure subsystem 113. Further, upon application of reduced pressure, the porous foam-like nature of the dressing bolster 114 as described above may permit the dressing bolster 114 to contract and apply a compressive force capable of closing a wound at a tissue site, such as the incision 104 at the tissue site 102.

In one embodiment, a comfort layer 124 may be coupled to the first side 120 of the dressing bolster 114. For example, the comfort layer 124 may be coupled to the dressing bolster 114 by a heat bond 125, or any other suitable technique. The comfort layer 124 may provide for patient comfort when the dressing bolster 114 is placed adjacent to the epidermis 106 of the patient. The comfort layer 124 may be any material for preventing skin irritation and discomfort while allowing fluid transmission through the comfort layer 124. As a non-limiting example, a woven elastic material or a polyester knit textile substrate may be used. As another non-limiting example, an InterDry™ textile material from Milliken Chemical of Spartanburg, S.C., may be used. The comfort layer 124 may include anti-microbial substances, such as silver.

As used herein, the term "coupled" may include coupling via a separate object and direct coupling. The term "coupled" may also encompass two or more components that are continuous with one another by virtue of each of the components being formed from the same piece of material. Also, the term "coupled" may include chemical, such as via a chemical bond, mechanical, thermal, or electrical coupling. Fluid coupling means that fluid may be in communication between the designated parts or locations.

Continuing with FIGS. 1-3, the retention pouch 116 may include a first permeable layer 126, a second permeable layer 127, and an absorbent core 128. In one embodiment, the absorbent core 128 may be encapsulated between the first permeable layer 126 and the second permeable layer 127. The first permeable layer 126 may have edges 126a,b coupled respectively to edges 127a,b of the second permeable layer 127 around or otherwise encapsulating the absorbent core 128. The edges 126a,b and 127a,b of the first and the second permeable layers 126, 127 may be secured or coupled to one another in any suitable manner, such as, for example, by the heat bond 125 described above.

The retention pouch 116 may be adapted to retain fluid, such as fluid extracted from the tissue site 102. The first permeable layer 126 and the second permeable layer 127 may each have a fluid acquisition surface 129 facing in an opposite direction from a directional wicking surface 130. The directional wicking surfaces 130 of the first and the second permeable layers 126, 127 may each have a grain (not shown) oriented in a longitudinal direction along the length of the reduced-pressure dressing 112. The orientation of the grain of the directional wicking surfaces 130 may facilitate the wicking of fluid, such as fluid extracted from the tissue site 102, along the length of the reduced-pressure dressing 112. The wicking of fluid in this manner may enhance the ability of the retention pouch 116 to retain and manage fluid efficiently for preventing clogs as will be described in further detail below. The retention pouch 116 may additionally include a recess 131 capable of receiving or otherwise accommodating a filter 133. The filter 133 may be positioned in a gap 135 between the recess 131 and the sealing member 118 to further enhance the ability of the reduced-pressure dressing 112 to resist clogging. The recess 131 may be formed or defined, for example, by coupling the first permeable layer 126 to the second permeable layer 127 through the absorbent core 128. In another embodiment, a portion of the absorbent core 128 may be removed to provide, for example, a notch 138 or other aperture, permitting the first permeable layer 126 to contact and to be coupled to the second permeable layer 127. The first and the second permeable layer 126, 127 may be coupled, for example, by the heat bond 125 or other suitable technique.

The first and the second permeable layers 126, 127 may be any material exhibiting the fluid acquisition and wicking characteristics described above, such as, for example, Libeltex TDL2, manufactured by Libeltex. The filter 133 may be formed of any suitable hydrophobic material and may have a 3-dimensional shape.

The absorbent core 128 may be any material that retains liquids and may, for example, include one or more of the following: Luquafleece® material; BASF 402c; Technical Absorbents 2317, available from Technical Absorbents (www.techabsorbents.com); sodium polyacrylate super absorbers; cellulosics (carboxy methyl cellulose and salts such as sodium CMC); or alginates. The absorbent core 128 may allow fluids and exudate removed from the tissue site 102 to be stored within the retention pouch 116 rather than external to the reduced-pressure dressing 112.

Similar to the dressing bolster 114, the retention pouch 116 may include a plurality of flexibility notches 121 or recesses that may be lateral cuts in the retention pouch 116. The retention pouch 116 may include one or more longitudinal cuts or other cuts. The flexibility notches may enhance the flexibility of the retention pouch 116 and increase the ability of the retention pouch 116 to conform to, for example, the joint of a patient. Further, the enhanced flexibility may assist in preventing any interference with the ability of the dressing bolster 114 to contract as described above.

The retention pouch 116 may have a maximum fluid capacity. At the maximum fluid capacity of the retention pouch 116, fluid communication through the retention pouch 116 may be substantially precluded. The retention pouch 116 may have a maximum fluid capacity of any amount to suit a particular application. In one embodiment, for example, the retention pouch 116 may have a maximum fluid capacity of about 50 milliliters.

In one embodiment, the dressing bolster 114 may be positioned between the tissue site 102 and the retention pouch 116 with the first side 120 of the dressing bolster 114 facing the tissue site 102. In this embodiment, the fluid acquisition surface 129 of the first permeable layer 126 may be positioned proximate to and facing the second side 122 of the dressing bolster 114. Further, the fluid acquisition surface 129 of the second permeable layer 127 may be positioned facing the absorbent core 128.

The sealing member 118 may provide a fluid seal over the dressing bolster 114, the retention pouch 116, and at least a portion of the epidermis 106 of the patient. As such, the sealing member 118 may be formed from any material that allows for a fluid seal. "Fluid seal," or "seal," means a seal adequate to maintain reduced pressure at a desired site given the particular reduced pressure source or subsystem involved. The sealing member 118 may be sealed against the epidermis 106 or against a gasket or drape by a sealing apparatus. The sealing apparatus may be, for example, an adhesive sealing tape, drape tape or strip, double-side drape tape, pressure-sensitive adhesive, paste, hydrocolloid, hydrogel, or similar material. If a tape is used, the tape may be formed of the same material as the sealing member 118 with a pre-applied, pressure-sensitive adhesive. The pressure-sensitive adhesive or other sealing apparatus may be applied, for example, on a patient-facing side of the sealing-member 118, or portion thereof, for providing the fluid seal between the sealing member 118 and the epidermis 106. Before the sealing member 118 is secured to the epidermis, removable strips covering and protecting the pressure-sensitive adhesive may be removed.

In one embodiment, the sealing member 118 may be an elastomeric material that provides the fluid seal described above. "Elastomeric" means having the properties of an elastomer and generally refers to a polymeric material that has rubber-like properties. More specifically, an elastomeric material may have an ultimate elongation greater than 100% and a significant amount of resilience. The resilience of a material refers to the ability of the material to recover from an elastic deformation. Examples of elastomers and elastomeric materials may include, without limitation, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Further, the sealing member 118 may be, for example, a silicone drape, a 3M Tegaderm® drape, an acrylic drape such as one available from Avery Dennison, or an incise drape.

The sealing member 118 may include a first sealing member portion 132 and a second sealing member portion 134. The first sealing member portion 132 may extend over and beyond the retention pouch 116 and the dressing bolster 114 to form a sealing member extension 136. The sealing member extension 136 has a first side (not shown) and a second side (not shown), and the first side may be adapted to face inward toward the tissue site 102. The sealing member extension 136 may be, for example, a sealing member flange. A portion of the sealing member 118 may include a sealing member aperture 137 to allow fluid communication between the reduced-pressure dressing 112 and a reduced-pressure source, such as the reduced-pressure subsystem 113.

The first side of the sealing member extension 136 may be placed on a second side (not shown) of the second sealing member portion 134 that is adapted to face away from the tissue site 102. The sealing member extension 136 and the second side of the second sealing member portion 134 may be coupled, for example, by an adhesive, the previously described heat bond 125, welding, cements, or other suitable devices. In another embodiment, the first sealing member portion 132 and the second sealing member portion 134 may be integrally formed. The first sealing member portion 132 may include a plurality of bellows 142, folds, or stretch zones. The bellows 142 may provide additional material to enhance the ability of the sealing member 118 to stretch or to move. For example, if the reduced-pressure dressing 112 is used on a joint or other area of movement on a patient, additional material provided by the bellows 142 may enhance the ability of the sealing member 118 to move and conform to the joint.

One or more release members (not shown) may be releasably coupled to the second side of the second sealing member portion 134. The release members may provide stiffness and assist in deployment of the reduced-pressure dressing 112. The release members may be a casting paper or a film held on the second side of the second sealing member portion 134.

The reduced-pressure interface 119 may be coupled to the sealing member 118 and may be in fluid communication with the sealing member aperture 137 in the sealing member 118. The reduced-pressure interface 119 may provide fluid communication between the sealing member aperture 137 and the reduced-pressure delivery conduit 115. The reduced-pressure interface 119 may be formed as a component of a reduced-pressure assembly 140.

In one embodiment, the reduced-pressure interface 119 may include a membrane filter (not shown) in fluid communication with the sealing member aperture 137 for prevention of clogs and transmission of odors from the reduced-pressure dressing 112 during therapy. The membrane filter may be, for example, a hydrophobic or oleophobic filter. Additionally, the membrane filter may include a substance, such as, for example, charcoal for controlling odor. The membrane filter may be replaceable or formed integrally with the reduced-pressure interface 119 and the reduced-pressure assembly 140, if so equipped. In another embodiment, the membrane filter may be positioned in any suitable location between the reduced-pressure dressing 112 and a reduced-pressure source 144, described below.

The reduced-pressure subsystem 113 may include a reduced-pressure source 144. The reduced-pressure source 144 may provide reduced pressure as a part of the system 100. The reduced-pressure source 144 may be any suitable device for providing reduced pressure as described herein, such as, for example, a vacuum pump, wall suction, or other source. The reduced-pressure source 144 may be fluidly coupled to the reduced-pressure interface 119 by the reduced-pressure delivery conduit 115. The reduced-pressure interface 119 may deliver the reduced pressure through the sealing member aperture 137 of the sealing member 118 to the reduced-pressure dressing 112 and the tissue site 102.

As used herein, "reduced pressure" generally refers to a pressure less than the ambient pressure at the tissue site 102 being subjected to treatment. This reduced pressure may be less than the atmospheric pressure or less than a hydrostatic pressure at a tissue site. Unless otherwise indicated, values of pressure stated herein are gauge pressures. While the amount and nature of reduced pressure applied to a tissue site may vary according to the application, the reduced pressure may be between about −5 mm Hg to about −500 mm Hg, and more specifically, between about −100 mm Hg to about −200 mm Hg.

The reduced pressure delivered may be constant or varied, patterned or random, and may be delivered continuously or intermittently. Although the terms "vacuum" and "negative pressure" may be used to describe the pressure applied to a tissue site, the actual pressure applied to the tissue site may be more than the pressure normally associated with a complete vacuum. Consistent with the use herein, an increase in reduced pressure or vacuum pressure may refers to a relative reduction in absolute pressure.

In one embodiment, one or more monitoring devices (not shown) may be fluidly coupled to the reduced-pressure delivery conduit 115. The monitoring devices may be, for example, a pressure-feedback device, a volume detection system, a blood detection system, an infection detection system, a flow monitoring system, a temperature monitoring system, or other device. In another embodiment, the monitoring devices may be formed integrally with the reduced-pressure subsystem 113 and/or the reduced-pressure source 144.

The reduced-pressure treatment system 100 may include a fluid capacity indicator 145 capable of indicating whether the retention pouch 116 has reached maximum fluid capacity. The retention pouch 116 may communicates reduced pressure applied to the reduced-pressure dressing 112 to the fluid capacity indicator 145. In one embodiment, the fluid capacity indicator 145 may be a component of the reduced-pressure assembly 140. In another embodiment, the fluid capacity indicator 145 may be a separate unit in fluid communication with the retention pouch 116.

Referring now to FIGS. 4-11, the fluid capacity indicator 145 may be formed with a moving member 152 and a visual indicator 154 associated with the moving member 152. The moving member 152 may be adapted to move when reduced pressure communicated through the retention pouch 116 exceeds a threshold pressure ($P_t$).

In one embodiment, the visual indicator 154 is an indicator member 162, such as, for example, a disk-shaped member 164. The disk-shaped member 164 may also be a button or a member of any shape that indicates a changed state relative to pressure. The moving member 152 may be a collapsible wall 156 that has a first end 158 and a second end 160. The first end 158 may be coupled to the indicator member 162. The second end 160 may be coupled to a base 166. The collapsible wall 156 and the indicator member 162 form a pressure vessel with the base 166 or with the retention pouch 116. The collapsible wall 156 may have a convex interior surface 157 and may include baffles or other features to assist in collapsing the collapsible wall 156.

When reduced pressure delivered to the dressing bolster 114 and communicated through the retention pouch 116 to the fluid capacity indicator 145 exceeds the threshold pressure ($P_t$), the collapsible wall 156 may collapse. When the collapsible wall 156 collapses, the visual indicator 154 may move from a first position, such as an extended position shown in FIG. 5A, to a second position, such as a retracted position shown in FIG. 5B. The collapsible wall 156 of the fluid capacity indicator 145 may be sized and shaped to collapse or move the indicator member 162 substantially flush against the base 166 at the threshold pressure ($P_t$). When the threshold pressure ($P_t$) no longer exists, the visual indicator 154 may return to the extended position. At maximum fluid capacity, or when the retention pouch 116 is otherwise substantially saturated with fluid, the retention pouch 116 may preclude the communication of reduced pressure to the fluid capacity indicator 145. Thus, the threshold pressure may not exist, for example, when the retention pouch 116 is substantially saturated with fluid. Accordingly, when in the extended position during therapy, the visual indicator 154 may indicate that the retention pouch 116 and/or the reduced-pressure dressing 112 have reached the maximum fluid capacity.

The thickness of the collapsible wall 156, wall material stiffness, and wall geometry are examples of variables that may impact the pressure at which the collapsible wall 156 collapses. The rigidity of the base 166 may also be a factor. While the wall thickness of the collapsible wall 156 may be determined using finite element analysis, it may be necessary to empirically determine the wall thickness to achieve movement at the threshold pressure ($P_t$). In some embodiments, the collapsible wall 156 may be designed so that the collapsible wall 156 collapses by sudden buckling as the threshold pressure ($P_t$) is crossed, providing a binary indication of the fluid capacity within the reduced-pressure dressing 112.

The fluid capacity indicator 145 may be formed on the base 166 with the reduced-pressure interface 119 as a component of the reduced-pressure assembly 140. In such an embodiment, the fluid capacity indicator 145 may be in fluid communication with the retention pouch 116 through an indicator aperture 167. The fluid capacity indicator 145 may also be a separate component from the reduced-pressure indicator 119 and reduced-pressure assembly 140 that is placed into fluid communication with the retention pouch 116.

The fluid capacity indicator 145, reduced-pressure interface 119, and base 166 may be formed from a medical-grade, soft polymer or other pliable material. As non-limiting examples, the fluid capacity indicator 145, reduced-pressure interface 119, and base 166 may be formed from polyurethane, polyethylene, polyvinyl chloride (PVC), fluorosilicone, ethylene-propylene, or similar materials. In one illustrative, non-limiting embodiment, the fluid capacity indicator 145, reduced-pressure interface 119, and base 166 are molded from DEHP-free PVC. The fluid capacity indicator 145, reduced-pressure interface 119, and base 166 may be molded, casted, or extruded, and may be formed as an integral unit.

As previously described, the reduced-pressure interface 119 may be in fluid communication with the reduced-pressure delivery conduit 115 for delivering reduced pressure to the reduced-pressure dressing 112. In the illustrative, non-limiting embodiments shown in FIGS. 4-11, the reduced-pressure interface 119 may include a housing wall 176. The housing wall 176 may be dome-shaped or any shape that defines an interior space 178 that has an open portion, or interface aperture 180, in fluid communication with the sealing member aperture 137 in the reduced-pressure dressing 112.

Figure 9:
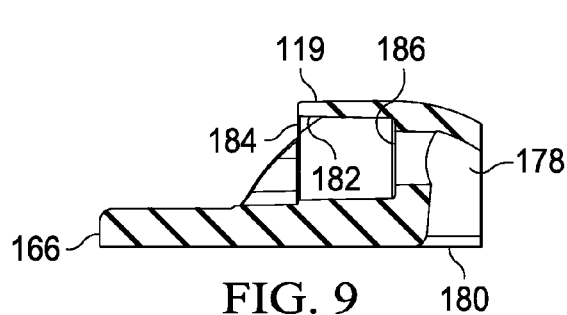
FIG. 9 is a cross-section view of the reduced-pressure assembly of FIG. 4 taken along line 9-9 in FIG. 6.
Figure 10:
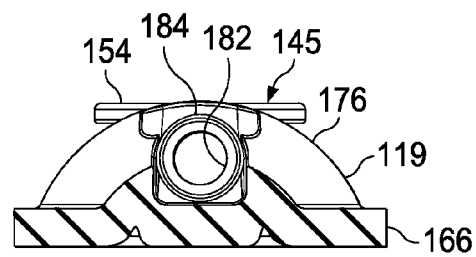
FIG. 10 is a cross-section view of the reduced-pressure assembly of FIG. 4 taken along line 10-10 in FIG. 6.
Figure 11:
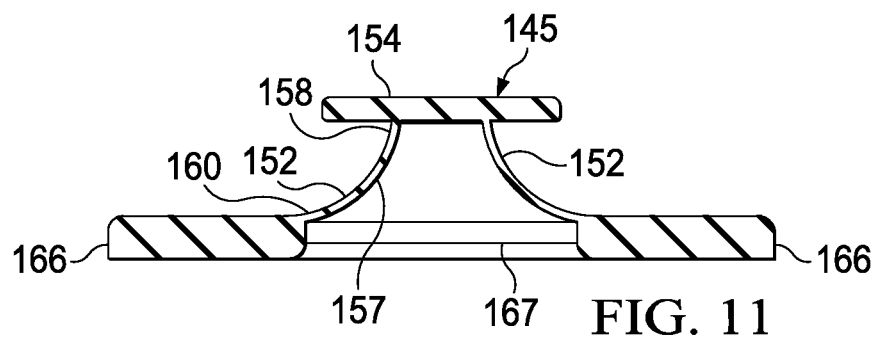
FIG. 11 is a cross-section view of the reduced-pressure assembly of FIG. 4 taken along line 11-11 in FIG. 6.

The housing wall 176 may have a receptacle 182 for receiving and maintaining an end of the reduced-pressure delivery conduit 115. As shown in FIGS. 9 and 10, the receptacle 182 may have a first aperture 184 and a second aperture 186 in fluid communication with one another. The first aperture 184 may be large enough to allow the reduced-pressure delivery conduit 115 to enter with an interference fit. The second aperture 186 may allow fluid to enter, but restrict the reduced-pressure delivery conduit 115 from entering. The first and the second apertures 184, 186 may be in fluid communication with the interior space 178.

Referring to the previously described embodiments of FIGS. 1-11, in one illustrative embodiment of operation, a user may place the first side 120 of the dressing bolster 114 proximate the tissue site 102. Further, the user may place the retention pouch 116 proximate the second side 122 of the dressing bolster 114. Subsequently, the user may place the sealing member 118 over the retention pouch 116, the dressing bolster 114, and a portion of the epidermis 106 of the patient. The sealing member 118 may be sealingly secured to the portion of the epidermis 106 as described above. The reduced-pressure delivery conduit 115 may be coupled to the reduced-pressure interface 119 and to the reduced-pressure source 144. In one embodiment, the reduced-pressure dressing 112 may be a pre-assembled component placed proximate to the tissue site 102 by the user.

The reduced-pressure source 144 may then be activated and for delivering reduced pressure to the reduced-pressure dressing 112. Upon application of the reduced pressure to the reduced-pressure dressing 112, the dressing bolster 114 may contract and distribute the reduced pressure to the tissue site 102. The contraction of the dressing bolster 114 may apply a compressive force capable of closing a portion of the tissue site 102, such as the incision 104. For example, the compressive force may have a first force component directed downward toward the tissue site 102 and a second force component directed laterally across the tissue site 102. The combination of the first and the second force components may cooperate, for example, to urge the sides of the incision 104 to a closed position.

As previously described, the dressing bolster 114 and the retention pouch 116 may be formed of permeable materials that act as a manifold for providing fluid communication between the sealing member aperture 137 and the tissue site 102. Thus, the reduced pressure distributed to the tissue site 102 by the dressing bolster 114 may draw fluid away from the tissue site 102 toward the retention pouch 116 where the fluid may be retained. As depicted by the fluid communication arrows 117 in FIG. 3, the sealing member aperture 137 may be in fluid communication with the edges 123 of the dressing bolster 114 along the sides of the reduced-pressure dressing 112. In this configuration, the reduced-pressure dressing 112 may not require fluid communication through the retention pouch 116 in order for reduced pressure applied the reduced-pressure dressing 112 to reach the tissue site 102. Accordingly, when the retention pouch 116 has reached the maximum fluid capacity, the reduced-pressure interface 119 may remain in fluid communication with the tissue site 102 at least by virtue of the fluid communication with the edges 123 of the dressing bolster 114. The fluid communication between the reduced-pressure interface 119 and the edges 123 may permit the dressing bolster 114 to distribute reduced pressure to the tissue site 102 if the retention pouch 116 becomes substantially saturated with fluid, or otherwise clogged. In such a configuration, the edges 123 of the dressing bolster 114 may provide an independent or direct fluid communication path between the reduced-pressure interface 119 and the tissue site 102. Thus, when the retention pouch 116 has reached the maximum fluid capacity, the reduced-pressure interface 119 may be in fluid communication with the tissue site 102 at least through an edge 123 of the dressing bolster 114.

The positioning of the dressing bolster 114 and the retention pouch 116 as a layer relative to one another, with the retention pouch 116 positioned above the dressing bolster 114 and away from the tissue site 102, may permit the dressing bolster 114 to contract freely without any interference. Further, the thickness of the retention pouch 116 relative to the dressing bolster 114 may provide additional benefit for the operation of the dressing bolster 114. For example, FIG. 3 depicts the dressing bolster 114 as having a thickness greater than a thickness of the retention pouch 116. Although the reduced-pressure dressing 112 does not require the retention pouch 116 to be thinner than the dressing bolster 114, such a configuration may enhance the ability of the dressing bolster 114 to operate freely without interference from fluid being absorbed by the retention pouch 116.

As described above, the retention pouch 116 may include the first and the second permeable layers 126, 127 that encapsulate the absorbent core 128 for retaining fluid during treatment. As shown in FIG. 3, the first permeable layer 126 may be positioned proximate the dressing bolster 114 and the second permeable layer 127 may be positioned proximate the sealing member 118. The fluid acquisition surface 129 of the first permeable layer 126 may face the dressing bolster 114 and the directional wicking surface 130 of the first permeable layer 126 may face the absorbent core 128. Further, the fluid acquisition surface 129 of the second permeable layer 127 may face the absorbent core 128 and the directional wicking surface 130 of the second permeable layer 127 may face the sealing member 118.

As fluid contacts the first and the second permeable layers 126, 127, the fluid may be distributed by each of the directional wicking surfaces 130 along the length of the reduced-pressure dressing 112. The grain of each of the directional wicking surfaces 130 may be oriented along the length of the reduced-pressure dressing 112 such that the fluid will follow the direction of the grain by a wicking action without regard to the orientation of the reduced-pressure dressing 112 on the patient. As such, the fluid may be distributed and absorbed by the absorbent core 128 in a substantially even manner.

The configuration of the first and second permeable layers 126, 127 may be particularly useful in managing fluid extracted from the tissue site 102 within the reduced-pressure dressing 112. In one embodiment, as fluid contacts the fluid acquisition surface 129 of the first permeable layer 126, the fluid may first be drawn into the retention pouch 116 and away from the dressing bolster 114. Subsequently, the fluid may be wicked along the directional wicking surface 130 of the first permeable layer 126 for absorption by the absorbent core 128. As fluid contacts the directional wicking surface 130 of the second permeable layer 127, the fluid may first be wicked along the directional wicking surface 130 of the second permeable layer 127, away from the sealing member aperture 137. Fluid contacting the second permeable layer 127 may first be wicked away from the sealing member aperture 137 to preclude clogging of the sealing member aperture 137. Clogging can occur, for example, from excess fluid near the sealing member aperture 137. Subsequently, the fluid may be drawn into the retention pouch 116 through the second permeable layer 127 and absorbed by the absorbent core 128. Thus, the configuration and positioning of the first and second permeable layers 126, 127 relative to one another may direct fluid away from the tissue site 102 and away from the sealing member aperture 137 for storage in the retention pouch 116. In this manner, the tissue site 102 may be kept substantially free of fluids, and the sealing member aperture 137 may be kept substantially free of clogs.

The recess 131 on the retention pouch 116 may further enhance the ability of the reduced-pressure dressing 112 to resist clogging. For example, the recess 131 may provide the gap 135 between the sealing member aperture 137, which may be in fluid communication with the reduced-pressure interface 119, and the retention pouch 116. The gap 135 may substantially preclude excess fluid from becoming lodged between the sealing member 118 and the retention pouch 116 near the sealing member aperture 137. As an additional precaution, the filter 133 may be positioned in the gap 135 to preclude excess fluids from reaching the sealing member aperture 137.

The storage and management of extracted fluids in the reduced-pressure dressing 112 may provide many benefits. The potential for clogging as discussed above may be reduced and the storage of fluids within the reduced-pressure dressing 112 may eliminate the need for external storage components that could potentially leak or cause discomfort. Further, the reduction in the number of components may lowers the volume that must be maintained at reduced pressure, thereby increasing efficiency. Also, the reduced-pressure dressing 112 may be capable of managing fluids without regard to any particular orientation of the reduced-pressure dressing 112 on the patient. Thus, the reduced-pressure dressing 112 at least provides increased comfort, usability, efficiency, and confidence that the patient is receiving effective treatment.

For operation, the fluid capacity indicator 145 may require that the reduced pressure being applied to the reduced-pressure dressing 112 be communicated through the retention pouch 116 to the fluid capacity indicator 145. The communication of reduced pressure through the retention pouch 116 to the fluid capacity indicator 145 may provide a pressure feedback signal to the fluid capacity indicator that is related to the fluid saturation of the retention pouch 116. Once the reduced pressure is greater, or more negative with respect to ambient pressure, than the threshold pressure ($P_t$), the fluid capacity indicator 145 may give a visual indication that the pressure has passed the threshold pressure ($P_t$). In this embodiment, when the threshold pressure ($P_t$) has been reached, the visual indicator 154 may move to a position substantially flush with, or otherwise near, the base 166. If reduced pressure is interrupted such that the threshold pressure ($P_t$) no longer persists, the visual indicator 154 may return to a position indicating a lack of adequate reduced pressure. Such an interruption in the reduced pressure could occur, for example, if the retention pouch 116 becomes substantially saturated with fluid, thereby precluding or otherwise inhibiting the communication of reduced pressure to the fluid capacity indicator 145. Thus, the physical position of the visual indicator 154 provides an indication as to the level of fluid saturation or capacity within the retention pouch 116 that may be easily understood by the user.

Figure 12:
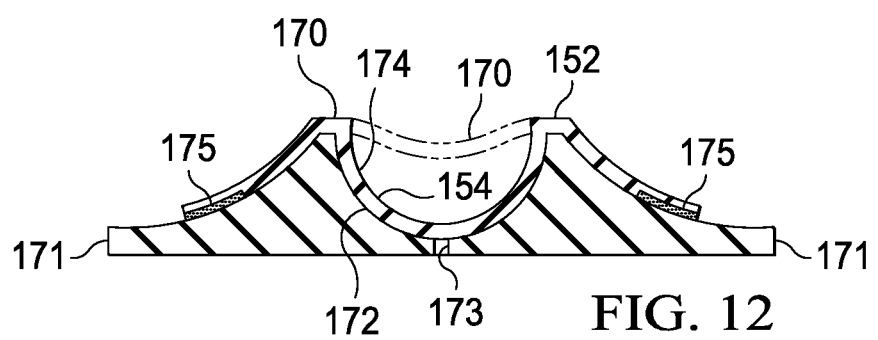
FIG. 12 is a cross-section view of another illustrative, non-limiting embodiment of a fluid capacity indicator.

Referring to FIG. 12, another embodiment is illustrated for the fluid capacity indicator 145. As shown in FIG. 12, the moving member 152 may be an indicator sealing member 170 suspended over a convex member 172. The convex member 172 may be formed in a base or body 171 having an aperture 173 in fluid communication with the retention pouch 116. The indicator sealing member 170 may be coupled to the convex member 172 by an adhesive 175 or other sealing device. The broken lines show the indicator sealing member 170 in a first position before the threshold pressure ($P_t$) has been achieved, and the solid lines show the indicator sealing member 170 in a position approximating the convex member 172 after the threshold pressure ($P_t$) has been achieved.

Continuing with the embodiment of FIG. 12, the visual indicator 154 may be a combination of elements. If the indicator sealing member 170 is a first color and a surface 174 is a second color, the combination may visually create a third color indicative of the threshold pressure ($P_t$) being achieved. In another embodiment, the indicator sealing member 170 may be slightly opaque at a distance, but when brought into contact with the surface 174 may allow visual indicia on the surface 174 to be read.

The color changes and indicia schemes for the visual indicator 154 mentioned in connection with FIG. 12 may also be utilized as an aspect of the illustrative embodiment of FIGS. 1-11. In addition or as an alternative, the moving member 152 may create an audible sound when going from a first position to a second position to signify audibly a change in state. For example, a "click" noise may be made as the moving member 152 goes from a retracted position to an extended position and vice-versa.

Figure 13:
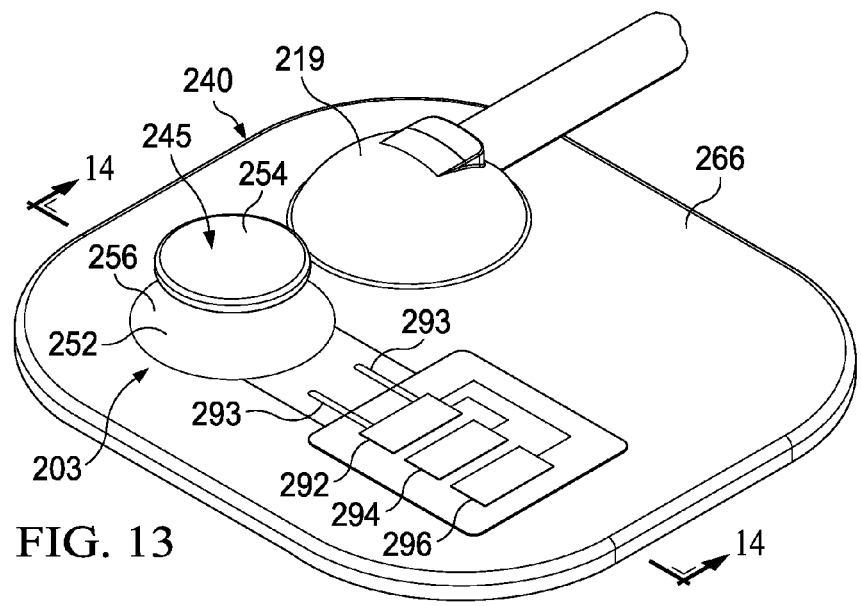
FIG. 13 is a perspective view of another illustrative embodiment of a reduced-pressure assembly with an electro-mechanical indicator.
Figure 14A:
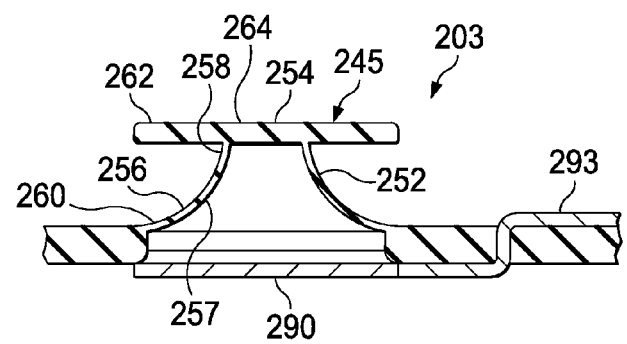
FIG. 14A is a cross-section view of a portion of an illustrative embodiment of a fluid capacity indicator depicted in FIG. 13, taken along line 14-14, and shown in the extended position.
Figure 14B:
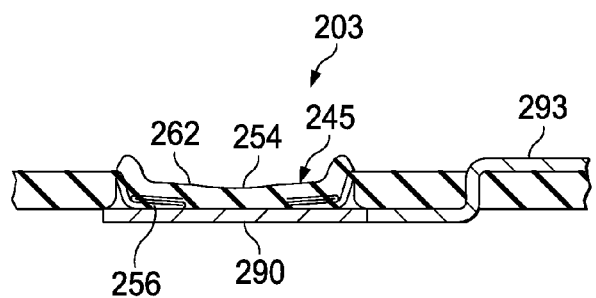
FIG. 14B is a cross-section view of a portion of an illustrative embodiment of a fluid capacity indicator depicted in FIG. 13, taken along line 14-14, and shown in the retracted position.

FIGS. 13-14B depict another illustrative embodiment of a reduced-pressure assembly 240 that may be used with a reduced-pressure system, such as the reduced-pressure treatment system 100 of FIG. 1. As shown in FIG. 13, the reduced-pressure assembly 240 may include a base 266 having a reduced-pressure interface 219 and a fluid capacity indicator 245. The reduced-pressure assembly 240 may be similar to the reduced-pressure assembly 140 of FIGS. 1-11. However, the fluid capacity indicator 245 associated with the reduced-pressure assembly 240 may be an electro-mechanical indicator 203. The electro-mechanical indicator 203 may provide a visual indication if the threshold pressure ($P_t$) does not exist, and may also provide a powered visual alert, an audible alert, or an output signal for other use. Although FIG. 13 depicts the electro-mechanical indicator 203 as a component of the reduced-pressure assembly 240, the electro-mechanical indicator 203 may be a separate component.

The electro-mechanical indicator 203 may be formed with a moving member 252 and a visual indicator 254 associated with the moving member 252. Similar to the embodiments of FIGS. 1-11, the moving member 252 may be adapted to move when reduced pressure communicated through the retention pouch 116 exceeds a threshold pressure ($P_t$). The visual indicator 254 may help a user to visualize the movement of the moving member 252. In one embodiment, the visual indicator 254 may be an indicator member 262, such as, for example, a disk-shaped member 264. The disk-shaped member 264 may also be a button or a member of any shape that signifies a changed state relative to pressure.

The moving member 252 may be a collapsible wall 256 that has a first end 258 and a second end 260. The first end 258 may be coupled to the indicator member 262. The second end 260 may be coupled to the base 266. The collapsible wall 256 and the indicator member 262 may form a pressure vessel with the base 266 or with the retention pouch 116. The collapsible wall 256 may have a convex interior surface 257 and may include baffles or other features to assist in collapsing the collapsible wall 256.

The electro-mechanical indicator 203 may additionally include a thin, tactile pressure transducer 290 associated with the moving member 252 and the visual indicator 254. When the moving member 252 collapses under reduced pressure, the tactile pressure transducer 290 may receive adequate physical pressure or contact to create an indication signal indicating that the reduced pressure has met or exceeded the threshold pressure ($P_t$). The tactile pressure transducer 290 may function to give a binary signal or may give a graduated signal, such as a voltage that varies with the magnitude of the force or pressure.

The tactile pressure transducer 290 may communicate with a detector circuit 292. One or more electrical leads 293 may be used to electrically couple the tactile pressure transducer 290 to the detector circuit 292. The detector circuit 292 may use the indication signal to provide an alert when appropriate. The detector circuit 292 may be a battery-powered electrical circuit that has been miniaturized. Numerous other circuits are possible.

When the reduced pressure is at the threshold pressure ($P_t$), or more negative relative to ambient pressure than the threshold pressure ($P_t$), the moving member 252 may move or collapse, causing a physical force to impinge on the tactile pressure transducer 290. The physical force on the tactile pressure transducer 290 may cause the indication signal to change states. The change in the indication signal may then be used to energize or de-energize an LED 294 or other powered visual device to provide a visual or audible signal to a user. In addition or as an alternative, the change in the indication signal may cause a speaker 296, or other transducer, such as a piezo-electric device, to be energized or de-energized to give a visual or an audible alert.

The tactile pressure transducer 290 may be any transducer or device that can detect that the moving member 252 has moved. The tactile pressure transducer 290 may be, as non-limiting examples, a piezoresistive strain gage, capacitive device, electromagnetic device, piezoelectric device, optical device, potentiometric device, or similar device. The tactile pressure transducer 290 may also include an integrated contact switch and a circuit that detects an open or closed state in response to movement of the moving member 252. In one illustrative, non-limiting embodiment, a thin-film resistive force sensor may be used, such as, for example, a FlexiForce® load sensor, available from Tekscan, Inc. of Boston, Mass. (www.tekscan.com).

Any suitable circuit design may be used as the detector circuit 292. For example, in one illustrative, non-limiting embodiment, the detector circuit 292 may use a P-channel MOSFET (PFET). In this illustrative embodiment, when the tactile pressure transducer 290 is exposed to pressure, the impedance of the tactile pressure transducer 290 may drop to a low value. Without pressure, the tactile pressure transducer 290 may have a high impedance. The LED 294 may be tied to the drain of the PFET so that when the PFET is off, there is no current through the LED. Thus, the PFET may act as an open switch. The tactile pressure transducer 290 may be used as part of a voltage divider to drive the gate of the PFET. When the tactile pressure transducer 290 is exposed to pressure, the impedance of the tactile pressure transducer 290 may be low and the voltage divider may change to a high voltage, which biases the PFET off. In the absence of pressure, the impedance of the tactile pressure transducer 290 may be high and the voltage divider may change to a low voltage, which biases the PFET on such that the LED will illuminate. A coin cell battery (not shown) may be mounted on the base 266 to power the detector circuit 292. The detector circuit 292 may be a flexible member to facilitate comfort of the patient. Other circuits may be readily used, and the components may be sterilized.

In another illustrative, non-limiting embodiment, the tactile pressure transducer 290 may develop an analog voltage signal. In this embodiment, the detector circuit 292 may be a comparator circuit to drive the previously described visual alert or audio alert. In another illustrative, non-limiting embodiment, the tactile pressure transducer 290 may develop an analog voltage signal and the detector circuit 292 may provide a number of alerts based on the sensed analog voltage. For example, a green light may be displayed when the reduced pressure is greater than the threshold pressure ($P_t$), and a yellow light may be displayed when the reduced pressure is lower than the threshold pressure ($P_t$), but not lower than an alarm pressure. A red light may be displayed when the reduced pressure is lower than an alarm pressure. As the level of fluid saturation in the retention pouch 116 increases, the communication of reduced pressure may decrease through the retention pouch 116 to the fluid capacity indicator 254 associated with the tactile pressure transducer 290. Thus, the decrease in communication of reduced pressure may correspond to an increase in pressure, or a pressure that is less negative relative to ambient pressure, that permits the fluid capacity indicator 254 to return to an extended position as described above. Thus, the state of pressure indicated by each of the alerts may indicate different degrees of fluid saturation of the retention pouch 116.

The use of the electro-mechanical indicator 203 may be particularly helpful in certain circumstances. For example, the electro-mechanical indicator 203 may alert a patient who is sleeping of a problem that might otherwise not be apparent. The electro-mechanical indicator 203 may simplify the visual reading or interpretation of the visual indicator 254.

Figure 15A:
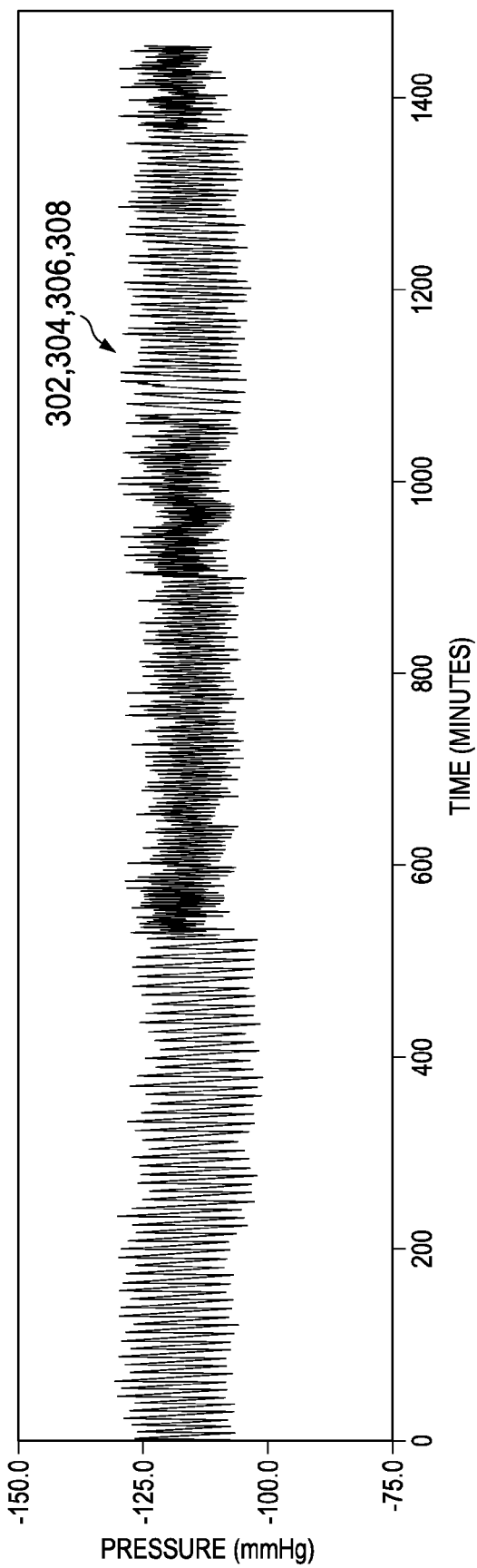

Referring to FIGS. 15A-15E, charts are provided that illustrate reduced pressure measured over a 24 hour period (1440 minutes) at four locations in the reduced pressure dressing 112 during an experimental treatment session for simulating extraction of fluid from a simulated tissue site. Reduced pressure (measured in mm HG) is plotted on the vertical axis and time (measured in minutes) is plotted on the horizontal axis. FIGS. 15A-15E provide plot lines depicting a different location 302, 304, 306, and 308 in the reduced-pressure dressing 112 at which reduced pressure was measured during the treatment session. FIG. 15A depicts each location 302, 304, 306, and 308 plotted together and FIGS. 15B-15E each depict one location 302, 304, 306, and 308, respectively. Thus, FIGS. 15A-15E illustrate the application of reduced pressure to a simulated tissue site during operation of the reduced-pressure dressing 112.

Beginning with a dry, unsaturated reduced-pressure dressing 112, fluid was instilled at a rate of at 2.083 milliliters per hour in the reduced-pressure dressing 112. A maximum volume of 50 milliliters of fluid was instilled in the reduced-pressure dressing 112 and ultimately absorbed by the retention pouch 116, described above, during the simulation. Reduced pressure was applied to the reduced-pressure dressing 112 while the fluid was being instilled in a central location on the underside of the reduced-pressure dressing 112. For a 1440 minute time frame, reduced pressure in the reduce-pressure dressing 112 was monitored at the locations 302, 304, 306, and 308 equidistantly spaced on the underside of the reduced-pressure dressing 112.

Variations in reduced pressure measured at the locations 302, 304, 306, and 308 are based, in part, on the effect of the fluid entering the reduced-pressure dressing 112. Each of the locations 302, 304, 306, and 308 for up to the 1440 minutes plotted maintained a reduced pressure ranging between about 110 mmHg and 130 mmHg. Thus, FIGS. 15A-15E show that the reduced-pressure dressing 112 effectively maintained reduced pressure to the locations 302, 304, 306, and 308 even when the retention pouch 116 reached a maximum fluid saturation of 50 milliliters near the end of the simulation. Accordingly, the retention of fluid in the reduced-pressure dressing 112 will not interfere with the application of reduced pressure to a tissue site, such as the tissue site 102, or with the operation of the reduced-pressure dressing 112.

Provided herein is also a method of manufacturing a dressing for use with reduced pressure to treat a tissue site on a patient. In one illustrative, non-limiting embodiment, a method of manufacturing the reduced-pressure dressing 112 may include the steps of providing the previously described dressing bolster 114. Further, the method may include the step of positioning the previously described retention pouch 116 proximate to the second side 122 of the dressing bolster 114. Subsequently, the method may include the step of positioning the sealing member 118 over the dressing bolster 114 and the retention pouch 116. The sealing member 118 may be adapted as previously described to sealingly engage the epidermis 106 of a patient that is proximate to the tissue site 102. Additionally, the method may include the step of fluidly coupling the reduced-pressure source 144 to the sealing member 118 such that the reduced pressure source 144 is in fluid communication with the dressing bolster 114 and the retention pouch 116.

In another embodiment, the step of positioning the retention pouch 116 may include the steps of positioning the first permeable layer 126 proximate to the second side 122 of the dressing bolster 114, providing the absorbent core 128, providing the second permeable layer 127, and encapsulating the absorbent core 128 between the first and second permeable layers 126, 127.

In another embodiment, the method may additionally include the step of forming the recess 131 on the retention pouch 116. The recess 131 may provide a gap 135 between the sealing member 118 and the retention pouch 116 that is proximate to the sealing member aperture 137. The reduced-pressure source 144 may be in fluid communication with the reduced-pressure dressing 112 through the sealing member aperture 137. Thus, the gap 135 may be proximate to the coupling of the reduced-pressure source 144 to the sealing member 118. The method may additionally include the step of positioning a filter 133 in the gap 135.

In another embodiment, the method may additionally include the step of fluidly coupling the previously described fluid capacity indicator 145 to the sealing member 118.

In another embodiment, the method may additionally include the step of providing a tactile pressure transducer 290 associated with the collapsible wall 156 and operable to provide a signal indicative of contact with the collapsible wall 156.

Although this disclosure has been provided in the context of certain illustrative, non-limiting embodiments, various changes, substitutions, permutations, and alterations may be made without departing from the scope of this disclosure as defined by the appended claims. Further, any feature described in connection with any one embodiment may also be applicable to any other embodiment.

What is claimed is:

1. A dressing for treating a tissue site, comprising:
   a dressing bolster adapted to be positioned proximate to the tissue site;
   a retention pouch positioned proximate the dressing bolster and in fluid communication with the dressing bolster, the retention pouch comprising a first permeable layer, a second permeable layer, and an absorbent core, the absorbent core being encapsulated between the first and the second permeable layer;
   a sealing member adapted to cover the retention pouch and the dressing bolster and to provide a fluid seal between the dressing and the tissue site, the first permeable layer positioned proximate the dressing bolster and the second permeable layer positioned proximate the sealing member; and
   an interface coupled to the sealing member and adapted to be in fluid communication with the dressing bolster;
   wherein a portion of the second permeable layer is indented to define a gap between the sealing member and the retention pouch.

2. The dressing of claim 1, wherein upon application of a reduced pressure to the dressing, the dressing bolster is adapted to contract and to apply a compressive force capable of closing an incision at the tissue site.

3. The dressing of claim 1, wherein the dressing bolster is comprised of a hydrophobic material adapted to distribute a reduced pressure to the tissue site.

4. The dressing of claim 1, wherein the dressing bolster is adapted to be positioned between the tissue site and the retention pouch.

5. The dressing of claim 1, wherein the first permeable layer and the second permeable layer each comprise a fluid acquisition surface and a directional wicking surface, the fluid acquisition surface facing an opposite direction from the directional wicking surface, wherein the fluid acquisition surface of the first permeable layer is positioned facing the dressing bolster and the fluid acquisition surface of the second permeable layer is positioned facing the absorbent core.

6. The dressing of claim 5, wherein the directional wicking surface of the first and the second permeable layer each have a grain oriented in a longitudinal direction along a length of the dressing, the directional wicking surface of the first and the second permeable layer being oriented to direct fluid along the length of the dressing.

7. The dressing of claim 1, further comprising a filter positioned in the gap.

8. The dressing of claim 1, wherein the dressing bolster and the retention pouch provide fluid communication between the interface and the tissue site, and wherein when the retention pouch has reached a maximum fluid capacity, the interface is in fluid communication with the tissue site at least through an edge of the dressing bolster.

9. The dressing of claim 1, wherein the portion of the second permeable layer that is indented is coupled to the first permeable layer.

10. A system for treating a tissue site of a patient, comprising:
    a dressing, comprising:
      a dressing bolster having a first side and a second side, the first side facing opposite the second side, wherein the first side of the dressing bolster is adapted to be positioned facing the tissue site,
      a retention pouch positioned proximate to the second side of the dressing bolster, the retention pouch adapted to retain a fluid and comprising a first permeable layer, a second permeable layer, and an absorbent core, wherein the absorbent core is encapsulated between the first and the second permeable layer,
      a sealing member adapted to cover the retention pouch, the dressing bolster, and a portion of an epidermis of the patient proximate to the tissue site, the sealing member having a sealing member aperture, and
      an interface coupled to the sealing member, the interface in fluid communication with the dressing through the sealing member aperture;
      wherein a portion of the second permeable layer is indented to define a gap between the sealing member aperture and the retention pouch;
    a reduced-pressure source; and
    a delivery conduit for fluidly coupling the reduced-pressure source to the interface.

11. The system of claim 10, wherein upon application of a reduced pressure to the dressing, the dressing bolster is adapted to contract and to apply a compressive force capable of closing an incision at the tissue site.

12. The system of claim 10, wherein the dressing bolster is comprised of a hydrophobic material adapted to distribute a reduced pressure to the tissue site.

13. The system of claim 10, wherein the first permeable layer is positioned proximate the dressing bolster and the second permeable layer is positioned proximate the sealing member.

14. The system of claim 13, wherein the first permeable layer and the second permeable layer each comprise a fluid acquisition surface and a directional wicking surface, the fluid acquisition surface facing an opposite direction from the directional wicking surface, wherein the fluid acquisition surface of the first permeable layer is positioned facing the dressing bolster and the fluid acquisition surface of the second permeable layer is positioned facing the absorbent core.

15. The system of claim 14, wherein the directional wicking surface of the first and the second permeable layer each have a grain oriented in a longitudinal direction along a length of the dressing, the directional wicking surface of the first and the second permeable layer being oriented to direct fluid along the length of the dressing.

16. The system of claim 10, further comprising a filter positioned in the gap.

17. The system of claim 10, wherein the dressing bolster and the retention pouch provide fluid communication between the interface and the tissue site, and wherein when the retention pouch has reached a maximum fluid capacity, the interface is in fluid communication with the tissue site at least through an edge of the dressing bolster.

18. The system of claim 10, wherein the indented portion of the second permeable layer is coupled to the first permeable layer.

19. The system of claim 10, further comprising a fluid capacity indicator, the fluid capacity indicator comprising:
    a moving member adapted to move under a reduced pressure communicated through the retention pouch; and
    a visual indicator associated with the moving member.

20. The system of claim 19, wherein:
    the moving member comprises a collapsible wall having a first end and a second end;

the visual indicator comprises an indicator member coupled to the first end of the collapsible wall, the indicator member having an extended position and a retracted position;

the collapsible wall is adapted to collapse under a reduced pressure greater than a threshold pressure ($P_t$); and the dressing further comprises a base coupled to the second end of the collapsible wall, the base being coupled to the sealing member.

21. The system of claim 19, wherein when the retention pouch has reached a maximum fluid capacity, the retention pouch substantially precludes the communication of the reduced pressure to the fluid capacity indicator.

22. The system of claim 10, wherein the dressing bolster is positioned between the tissue site and the retention pouch.

23. A method of manufacturing a dressing for treating a tissue site, the method comprising:

providing a dressing bolster having a first side and a second side, the first side facing opposite the second side, wherein the dressing bolster is adapted to distribute reduced pressure to the tissue site and to contract upon application of reduced pressure;

providing a first permeable layer, a second permeable layer, and an absorbent core;

encapsulating the absorbent core between the first permeable layer and the second permeable layer to form a retention pouch;

forming an indentation in a portion of the second permeable layer of the retention pouch;

positioning the first permeable layer of the retention pouch proximate to the second side of the dressing bolster; and covering the dressing bolster and the retention pouch with a sealing member, the second permeable layer being positioned proximate to the sealing member with the indented portion of the second permeable layer defining a gap between the sealing member and the retention pouch, a portion of the sealing member being adapted to sealingly engage an epidermis proximate to the tissue site.

24. The method of manufacturing of claim 23, wherein the first permeable layer and the second permeable layer each have an edge, and wherein encapsulating the absorbent core between the first permeable layer and the second permeable layer comprises coupling the edge of the first permeable layer to the edge of the second permeable layer around the absorbent core.

25. The method of manufacturing of claim 23, wherein the first permeable layer and the second permeable layer each comprise a fluid acquisition surface and a directional wicking surface, the fluid acquisition surface facing an opposite direction from the directional wicking surface, the method further comprising positioning the fluid acquisition surface of the first permeable layer facing the dressing bolster and positioning the fluid acquisition surface of the second permeable layer facing the absorbent core.

26. The method of manufacturing of claim 25, further comprising orienting the directional wicking surface of the first and the second permeable layer to direct fluid in a longitudinal direction along a length of the dressing.

27. The method of manufacturing of claim 23, further comprising positioning a filter in the gap.

28. A dressing for treating a tissue site of a patient, comprising:

a dressing bolster adapted to be positioned proximate to the tissue site;

a retention pouch positioned proximate the dressing bolster and in fluid communication with the dressing bolster, the retention pouch comprising a first permeable layer, a second permeable layer, and an absorbent core;

a sealing member adapted to cover the retention pouch and the dressing bolster and to provide a fluid seal between the dressing and the tissue site, the first permeable layer positioned proximate the dressing bolster and the second permeable layer positioned proximate the sealing member;

wherein the retention pouch includes a portion where the absorbent core is removed to provide a notch allowing the first permeable layer to contact the second permeable layer.

29. The dressing of claim 28, wherein the dressing bolster and the retention pouch are adapted to move independently of each other under the application of reduced pressure.

* * * * *

UNITED STATES PATENT AND TRADEMARK OFFICE
CERTIFICATE OF CORRECTION

| | | |
|---|---|---|
| PATENT NO. | : 9,693,907 B2 | |
| APPLICATION NO. | : 13/954562 | |
| DATED | : July 4, 2017 | |
| INVENTOR(S) | : Christopher Brian Locke et al. | |

It is certified that error appears in the above-identified patent and that said Letters Patent is hereby corrected as shown below:

On the Title Page

Under abstract "29 Claims, 11 Drawing Sheets" should read -39 Claims, 11 Drawing Sheets- In the Claims Column 17, Line 61, delete the text beginning with "10. A system" through Column 20, Line 42, ending with "reduced pressure." and insert the following:

--10. The dressing of claim 1, further comprising a fluid capacity indicator, the fluid capacity indicator comprising:
 a moving member adapted to move under a reduced pressure communicated through the retention pouch; and
 a visual indicator associated with the moving member.

11. The dressing of claim 10, wherein:
 the moving member comprises a collapsible wall;
 the visual indicator comprises an indicator member coupled to the collapsible wall that has an extended position and a retracted position; and
 the collapsible wall is adapted to collapse under a reduced pressure greater than a threshold pressure ($P_t$).

12. The dressing of claim 10, wherein:
 the moving member comprises a collapsible wall having a first end and a second end;
 the visual indicator comprises an indicator member coupled to the first end of the collapsible wall, the indicator member having an extended position and a retracted position; and
 the dressing further comprises a base coupled to the second end of the collapsible wall, the base being coupled to the sealing member.

Signed and Sealed this
Twenty-seventh Day of August, 2019

Andrei Iancu
*Director of the United States Patent and Trademark Office*

13. The dressing of claim 10, wherein:
 the moving member comprises an indicator sealing member over a convex member having an interior surface with a first color; and
 the visual indicator comprises the indicator sealing member having a second color that changes appearance to a third color as the indicator sealing member approximates the interior surface of the convex member.

14. The dressing of claim 10, wherein the visual indicator comprises an electro-mechanical indicator.

15. The dressing of claim 10, wherein when the retention pouch has reached a maximum fluid capacity, the retention pouch substantially precludes the communication of the reduced pressure to the fluid capacity indicator.

16. A system for treating a tissue site of a patient, comprising:
 a dressing, comprising:
 a dressing bolster having a first side and a second side, the first side facing opposite the second side, wherein the first side of the dressing bolster is adapted to be positioned facing the tissue site,
 a retention pouch positioned proximate to the second side of the dressing bolster, the retention pouch adapted to retain a fluid and comprising a first permeable layer, a second permeable layer, and an absorbent core, wherein the absorbent core is encapsulated between the first and the second permeable layer,
 a sealing member adapted to cover the retention pouch, the dressing bolster, and a portion of an epidermis of the patient proximate to the tissue site, the sealing member having a sealing member aperture, and
 an interface coupled to the sealing member, the interface in fluid communication with the dressing through the sealing member aperture;
 wherein a portion of the second permeable layer is indented to define a gap between the sealing member aperture and the retention pouch;
 a reduced-pressure source; and
 a delivery conduit for fluidly coupling the reduced-pressure source to the interface.

17. The system of claim 16, wherein upon application of a reduced pressure to the dressing, the dressing bolster is adapted to contract and to apply a compressive force capable of closing an incision at the tissue site.

18. The system of claim 16, wherein the dressing bolster is comprised of a hydrophobic material adapted to distribute a reduced pressure to the tissue site.

19. The system of claim 16, wherein the first permeable layer is positioned proximate the dressing bolster and the second permeable layer is positioned proximate the sealing member.

20. The system of claim 19, wherein the first permeable layer and the second permeable layer each comprise a fluid acquisition surface and a directional wicking surface, the fluid acquisition surface facing an opposite direction from the directional wicking surface, wherein the fluid acquisition surface of the first permeable layer is positioned facing the dressing bolster and the fluid acquisition surface of the second permeable layer is positioned facing the absorbent core.

21. The system of claim 20, wherein the directional wicking surface of the first and the second permeable layer each have a grain oriented in a longitudinal direction along a length of the dressing, the directional wicking surface of the first and the second permeable layer being oriented to direct fluid along the length of the dressing.

22. The system of claim 16, further comprising a filter positioned in the gap.

23. The system of claim 16, wherein the dressing bolster and the retention pouch provide fluid communication between the interface and the tissue site, and wherein when the retention pouch has reached a maximum fluid capacity, the interface is in fluid communication with the tissue site at least through an edge of the dressing bolster.

24. The system of claim 16, wherein the indented portion of the second permeable layer is coupled to the first permeable layer.

25. The system of claim 16, further comprising a fluid capacity indicator, the fluid capacity indicator comprising:
    a moving member adapted to move under a reduced pressure communicated through the retention pouch; and
    a visual indicator associated with the moving member.

26. The system of claim 25, wherein:
    the moving member comprises a collapsible wall having a first end and a second end;
    the visual indicator comprises an indicator member coupled to the first end of the collapsible wall, the indicator member having an extended position and a retracted position;
    the collapsible wall is adapted to collapse under a reduced pressure greater than a threshold pressure ($P_t$); and
    the dressing further comprises a base coupled to the second end of the collapsible wall, the base being coupled to the sealing member.

27. The system of claim 25, wherein when the retention pouch has reached a maximum fluid capacity, the retention pouch substantially precludes the communication of the reduced pressure to the fluid capacity indicator.

28. The system of claim 16, wherein the dressing bolster is positioned between the tissue site and the retention pouch.

29. A method of manufacturing a dressing for treating a tissue site, the method comprising:
    providing a dressing bolster having a first side and a second side, the first side facing opposite the second side, wherein the dressing bolster is adapted to distribute reduced pressure to the tissue site and to contract upon application of reduced pressure;

providing a first permeable layer, a second permeable layer, and an absorbent core; encapsulating the absorbent core between the first permeable layer and the second permeable layer to form a retention pouch;

forming an indentation in a portion of the second permeable layer of the retention pouch;

positioning the first permeable layer of the retention pouch proximate to the second side of the dressing bolster; and covering the dressing bolster and the retention pouch with a sealing member, the second permeable layer being positioned proximate to the sealing member with the indented portion of the second permeable layer defining a gap between the sealing member and the retention pouch, a portion of the sealing member being adapted to sealingly engage an epidermis proximate to the tissue site.

30. The method of manufacturing of claim 29, wherein the first permeable layer and the second permeable layer each have an edge, and wherein encapsulating the absorbent core between the first permeable layer and the second permeable layer comprises coupling the edge of the first permeable layer to the edge of the second permeable layer around the absorbent core.

31. The method of manufacturing of claim 29, wherein the first permeable layer and the second permeable layer each comprise a fluid acquisition surface and a directional wicking surface, the fluid acquisition surface facing an opposite direction from the directional wicking surface, the method further comprising positioning the fluid acquisition surface of the first permeable layer facing the dressing bolster and positioning the fluid acquisition surface of the second permeable layer facing the absorbent core.

32. The method of manufacturing of claim 31, further comprising orienting the directional wicking surface of the first and the second permeable layer to direct fluid in a longitudinal direction along a length of the dressing.

33. The method of manufacturing of claim 29, further comprising positioning a filter in the gap.

34. The method of manufacturing of claim 29, further comprising:

fluidly coupling a fluid capacity indicator to the sealing member, wherein the fluid capacity indicator comprises:

a moving member adapted to move when a reduced pressure communicated through the retention pouch exceeds a threshold value ($P_t$); and a visual indicator associated with the moving member.

35. The method of manufacturing of claim 34, wherein the moving member comprises a collapsible wall, and wherein the visual indicator comprises an indicator member coupled to the collapsible wall that has an extended position and a retracted position.

36. The method of manufacturing of claim 35, further comprising associating a tactile pressure transducer with the collapsible wall that is operable to provide a signal indicative of contact with the collapsible wall.

37. The method of manufacturing of claim 34, wherein the retention pouch is adapted to substantially preclude the communication of the reduced pressure to the fluid capacity indicator when the retention pouch is at a maximum fluid capacity.

38. A dressing for treating a tissue site of a patient, comprising:
   a dressing bolster adapted to be positioned proximate to the tissue site;
   a retention pouch positioned proximate the dressing bolster and in fluid communication with the dressing bolster, the retention pouch comprising a first permeable layer, a second permeable layer, and an absorbent core;
   a sealing member adapted to cover the retention pouch and the dressing bolster and to provide a fluid seal between the dressing and the tissue site, the first permeable layer positioned proximate the dressing bolster and the second permeable layer positioned proximate the sealing member;
   wherein the retention pouch includes a portion where the absorbent core is removed to provide a notch allowing the first permeable layer to contact the second permeable layer.

39. The dressing of claim 38, wherein the dressing bolster and the retention pouch are adapted to move independently of each other under the application of reduced pressure.--